United States Patent
Spenser et al.

(10) Patent No.: US 8,545,544 B2
(45) Date of Patent: Oct. 1, 2013

(54) DELIVERY CATHETER WITH CONSTRAINING SHEATH AND METHODS OF DEPLOYING MEDICAL DEVICES INTO A BODY LUMEN

(75) Inventors: Benjamin Spenser, M.P. Hof Karmel (IL); Ronen Neeman, Givaataim (IL); Gonen Somekh, Karem Maharal (IL)

(73) Assignee: Gardia Medical Ltd., Caesarea (IL)

( * ) Notice: Subject to any disclaimer, the term of this patent is extended or adjusted under 35 U.S.C. 154(b) by 256 days.

(21) Appl. No.: 12/417,299

(22) Filed: Apr. 2, 2009

(65) Prior Publication Data

US 2009/0254169 A1  Oct. 8, 2009

Related U.S. Application Data

(60) Provisional application No. 61/042,137, filed on Apr. 3, 2008.

(51) Int. Cl.
*A61F 2/06* (2013.01)

(52) U.S. Cl.
USPC ......... 623/1.12; 623/1.11; 623/1.23; 606/200

(58) Field of Classification Search
USPC ............... 623/1.12, 1.23; 606/198, 108, 170, 606/194, 200; 604/164.05, 171, 358; 206/363, 206/364, 365, 440, 438, 497; 383/207
See application file for complete search history.

(56) References Cited

U.S. PATENT DOCUMENTS

| | | | | |
|---|---|---|---|---|
| 5,647,857 | A * | 7/1997 | Anderson et al. | 604/264 |
| 5,765,682 | A * | 6/1998 | Bley et al. | 206/363 |
| 6,019,787 | A | 2/2000 | Richard et al. | |
| 6,254,628 | B1 * | 7/2001 | Wallace et al. | 623/1.12 |
| 6,352,561 | B1 | 3/2002 | Leopold et al. | |
| 2003/0149467 | A1 * | 8/2003 | Linder et al. | 623/1.11 |
| 2006/0015171 | A1 | 1/2006 | Armstrong | |
| 2006/0089627 | A1 * | 4/2006 | Burnett et al. | 606/1 |
| 2007/0191865 | A1 | 8/2007 | Pappas | |
| 2009/0105653 | A1 | 4/2009 | Spenser et al. | |
| 2009/0105746 | A1 | 4/2009 | Spenser et al. | |

OTHER PUBLICATIONS

International Search Report for PCT Application No. PCT/IB09/05610 dated Oct. 2, 2009.

* cited by examiner

*Primary Examiner* — Gary Jackson
*Assistant Examiner* — Katrina Stransky
(74) *Attorney, Agent, or Firm* — Novak Druce Connolly Bove + Quigg LLP

(57) ABSTRACT

A delivery catheter includes a constraining sheath coupled to a distal end of the catheter, and a medical device, such as an embolic protection device (EPD) or a stent, constrained by the sheath. A wire may extend proximally from the constraining sheath and be coupled thereto. A proximal pulling force on the wire causes the wire to tear the constraining sheath, thereby releasing the medical device from a constrained configuration to an expanded configuration.

5 Claims, 5 Drawing Sheets

DELIVERY CATHETER WITH CONSTRAINING SHEATH AND METHODS OF DEPLOYING MEDICAL DEVICES INTO A BODY LUMEN

CROSS-REFERENCE TO RELATED APPLICATIONS

This application claims priority to U.S. Provisional Application Ser. No. 61/042,137, filed Apr. 3, 2008, the entire content of which is incorporated herein by reference.

TECHNICAL FIELD

The present invention is directed generally to delivery catheters with constraining sheaths and methods of delivering medical devices to a body lumen. More particularly, the present invention is directed to a delivery catheter having a constraining sheath for delivery of constrained medical devices, such as, for example, embolic protection devices.

BACKGROUND

For devices used in interventional cardiology and peripheral vascular procedures, such as a therapeutic or diagnostic medical device intravascular catheter, one of the most important design considerations is minimizing the outer diameter of such devices in order to facilitate delivery into vessels with decreasing vessel lumen diameter. This outer diameter is often referred to as the device "profile". These intravascular catheters frequently incorporate therapeutic devices at the distal end, such as inflatable balloons, expandable vascular stents or embolic protection devices (EPD) such as filters, and it is critical to design catheters which can accommodate these therapeutic devices in a radially collapsed, crimped or otherwise radially constrained configuration, while maintaining an acceptably "low-profile" delivery configuration.

Once these intravascular catheters have been introduced and the distal end of the catheter is properly positioned at the desired treatment site, the collapsed therapeutic device is released from its crimped or constrained condition, and permitted to expand to a larger diameter for the therapeutic purpose. Therapeutic devices deployed at the distal end of such interventional catheters often comprise self-expanding stent or EPD systems, which are constructed of various shape-memory alloys (e.g., nitinol) that expand into contact with the vessel wall upon release from the catheter due to their shape-memory properties.

Nitinol-based devices, such as an EPD, would typically be crimped or radially-collapsed into a low-profile diameter during the process of loading into the distal end of the catheter, and would be constrained in this collapsed configuration during introduction and delivery through the related vasculature. For catheter based delivery systems, this constraint is accomplished by use of a constraining sheath which overlies the collapsed therapeutic device loaded in the distal end of the delivery catheter. The therapeutic device is typically delivered to the vascular treatment site by relative longitudinal movement between the EPD and constraining sheath. This relative longitudinal movement, for example, is accomplished by either slidably retracting the constraining sheath to release a stationary EPD, or alternatively by pushing a moveable EPD out the distal end of a stationary constraining sheath, thereby deploying the self-expanding EPD into vessel wall apposition within the vessel lumen being treated.

When loading the EPD into the constraining sheath, the tendency for the loaded EPD to self-expand against the interior surface of the constraining sheath will generate sufficient frictional forces which help to stabilize the EPD in its loaded position at the distal of the catheter during navigation and delivery to the treatment site. However, the process of deploying the EPD into the vessel necessarily requires overcoming these frictional forces in order to release the self-expanding EPD by either proximally retracting a moveable constraining sheath, or by distally advancing a EPD out from the distal end of a stationary constraining sheath. These frictional forces generally increase as a function of collapsing the EPD into the smallest possible device profile for delivery and deployment.

Since the EPD is loaded at the distal end of the catheter, and in vivo deployment of the EPD is at a vascular location quite remote from the proximal end of the catheter being manipulated by the interventional vascular practitioner, virtually all of the forces applied to the EPD and constraining sheath must be transferred through the entire length of the delivery catheter to accomplish the deployment process. In the case of an EPD mounted to an independent, pre-deployed guidewire, for example, it may be very difficult to accomplish deployment, since the column strength of the guidewire at the tapered end where the EPD is attached will be very limited.

Thus, it would be desirable to provide an EPD delivery catheter having a constraining sheath design adapted for release of the constrained EPD in a manner which significantly minimizes the problem of force transfer. Since most of the forces exerted between the EPD and constraining sheath during deployment relate to overcoming friction associated with relative longitudinal movement between the sheath and constrained EPD, it would be desirable to provide a delivery catheter and method for release of the EPD from a constraining sheath which greatly reduces or eliminates these frictional forces. Furthermore, it would be desirable to provide an EPD delivery catheter and method that would allow simple EPD from a very low profile catheter.

The delivery tubes and methods of the present disclosure solve one or more of the problems set forth above.

SUMMARY OF THE INVENTION

According to one aspect of the invention, a delivery catheter has a constraining sheath with a proximal end coupled to a distal end of the delivery catheter and a free distal end. The constraining sheath holds the medical device in a constrained state. The delivery catheter further includes a wire coupled to the constraining sheath and having a free end section extending proximally therefrom. The wire has a cutting section or a cutting element, or is coupled to a cutting section or a cutting element. The cutting section or cutting element tears the constraining sheath longitudinally when a force pulling is applied proximally to the free end section, thereby releasing the therapeutic device from a constrained configuration to an expanded configuration.

Embodiments of the invention may include one or more of the following features. The wire may be coupled to the constraining sheath near a location where the constraining sheath is coupled to the distal end of the delivery catheter, and the wire extends distally therefrom over the free distal end of the constraining sheath and continues proximally toward a proximal end of the delivery catheter. The distal end of the constraining sheath may include a cut or notch engaging with the wire to facilitate tearing of the sheath by the wire when the wire is pulled proximally.

In one embodiment, the wire may have an end section disposed near the free distal end of the constraining sheath, wherein the end section has a cutting edge which cuts the constraining sheath proximally from the free distal end of the constraining sheath when the wire is pulled proximally.

In one embodiment, the constraining sheath may have spaced-apart holes arranged longitudinally from the free distal end of the constraining sheath, wherein the wire is threaded through the holes proximally starting from the free distal end. In another embodiment, the constraining sheath may include a pocket or passageway arranged longitudinally from the free distal end of the constraining sheath and the wire passes through the pocket or passageway proximally starting from the free distal end.

In one embodiment, the wire may have an end section attached to the free distal end of the constraining sheath, with the end section extending either outside or inside the constraining sheath proximally from the free distal end and tearing the constraining sheath longitudinally when the wire is pulled proximally. To facilitate and control tearing of the constraining sheath, the constraining sheath may include a longitudinally extending tear strip, with the end section of the wire attached to the tear strip.

The medical device may be an embolic protection device (EPD) or a stent.

These and other features and advantages of the present invention will become more readily appreciated from the detailed description of the invention that follows.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION

Figure 1A:
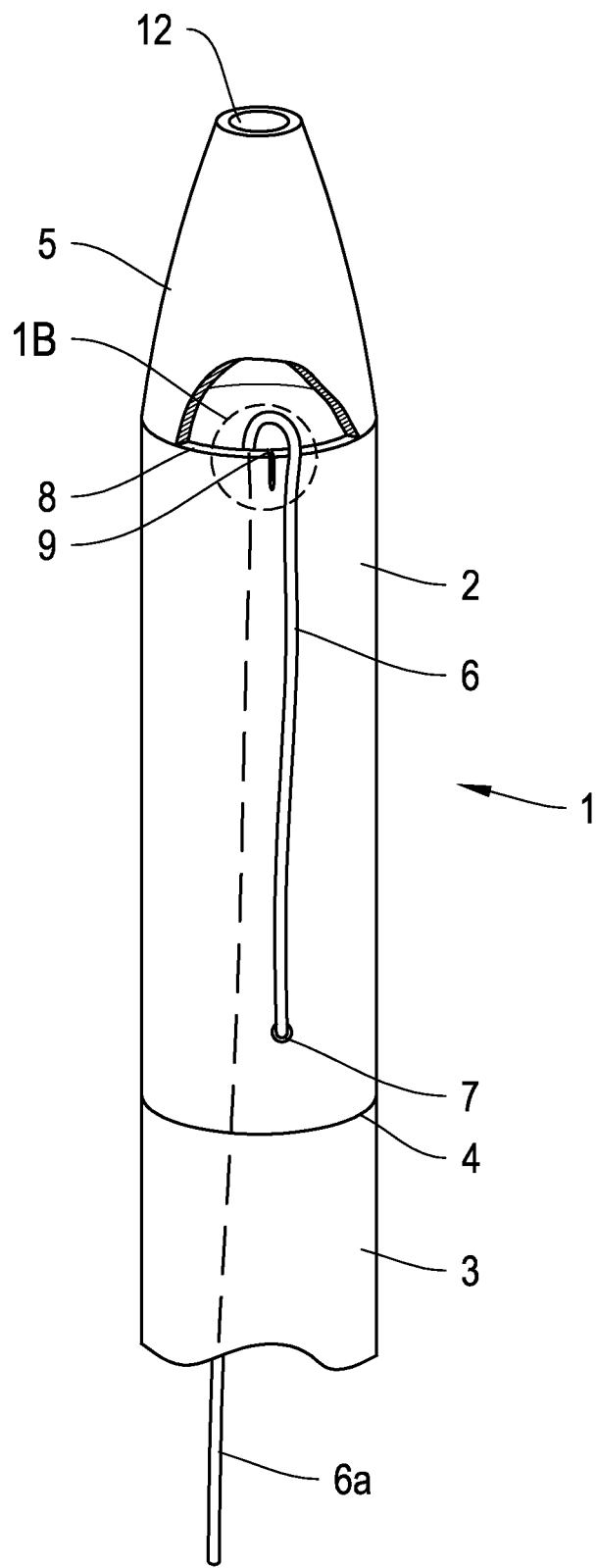
FIG. 1A is a diagrammatic view of an exemplary embodiment of a delivery tube in accordance with various aspects of the invention.

An exemplary embodiment of a delivery catheter 1 in accordance with the present disclosure is shown in FIG. 1A. FIG. 1A depicts a delivery catheter 1 having a shaft 3 with a distal end. The distal end of the shaft 3 may include a tapered tip 5 which may also be formed of relatively soft material which is atraumatic to the vessel being treated. A constraining sheath 2 is attached at the distal end of shaft 3 of the catheter 1. The constraining sheath 2 is adapted to receive a therapeutic device, such as an embolic protection device (EPD), which is not shown in FIG. 1. The therapeutic device is held inside the constraining sheath 2 in a collapsed configuration for later delivery and deployment into the vessel lumen being treated.

Also not shown in the drawings is a guidewire which extends in a conventional manner through opening 12 of tapered tip 5 and the unillustrated EPD. The guidewire is inserted into the vessel lumen typically past a treatment site, with the delivery catheter 1 and the EPD being advanced over the guidewire.

The EPD may be, for example, a filter which incorporates a guidewire locking mechanism of the type described in U.S. patent application Ser. No. 11/873,882, filed on Oct. 17, 2007, and entitled "Guidewire Stop," and U.S. patent application Ser. No. 11/873,893, filed on Oct. 17, 2007, and entitled "Guidewire Stop," the disclosures of which are incorporated herein by reference.

A pulling wire 6 may be coupled to the catheter 3, for example, at location 7 (FIG. 1A). Pulling wire 6 may be a flexible wire, and may comprise a metal wire or polymer suture, for example. Pulling wire 6 may extend distally from a region 7 of catheter shaft, where the constraining sheath 2 is proximally coupled to the distal end of shaft 3, to the distal rim 8 of the constraining sheath 2. From there, the pulling wire 6 is looped over the distal rim 8, returning for example inside the constraining sheath 2 and the shaft 3 proximally toward a proximal end of the catheter, as indicated by the reference symbol 6a. The trailing end 6a of the pulling wire may be accessible during use for actuation by the interventional vascular practitioner simply pulling the end 6a in a proximal direction to tear the constraining sheath 2 and effect release of the EPD from the delivery sheath 2.

Figure 2A:
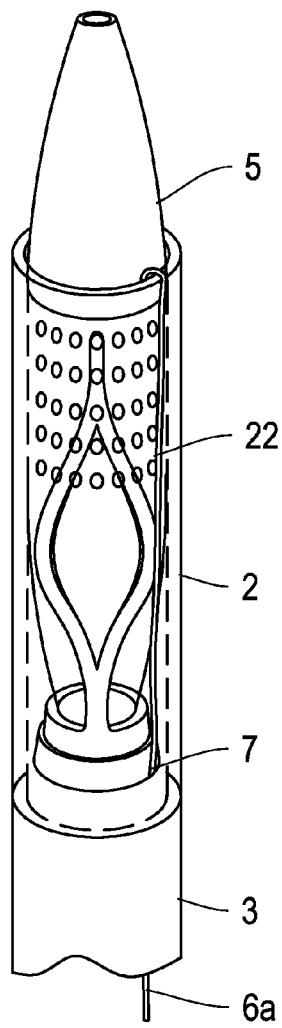
FIGS. 2A-2C show a diagrammatic view of the exemplary delivery tube of FIG. 1A, illustrating different stages of release of a constrained device from the delivery tube.
Figure 2B:
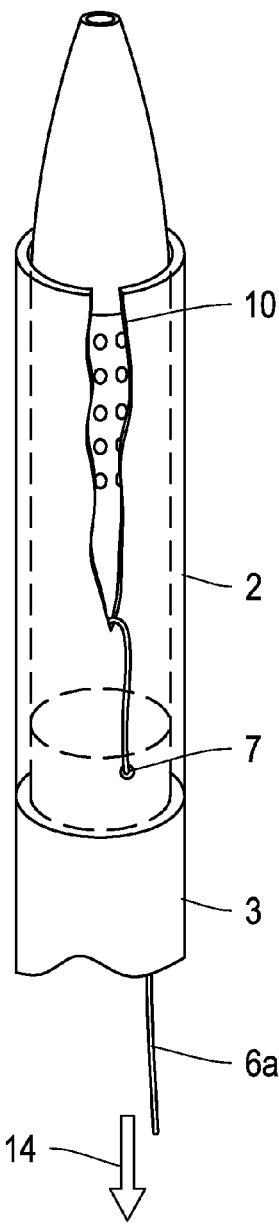
Figure 2C:
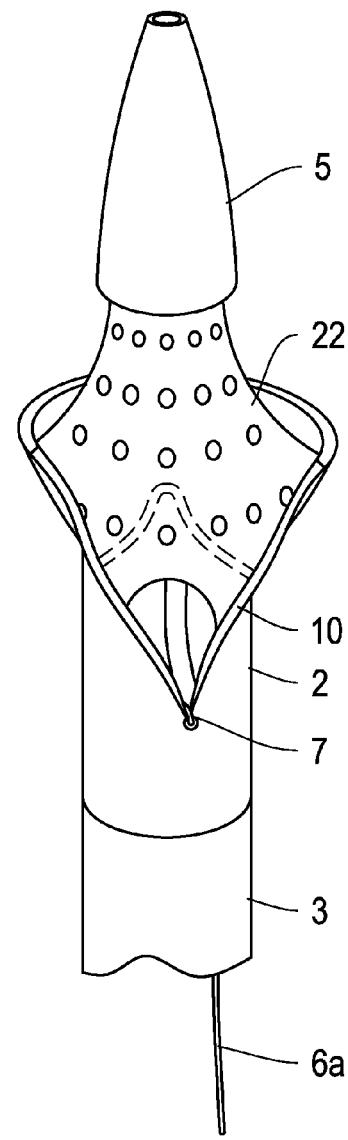

In operation, as illustrated in FIGS. 2A to 2C, once the delivery catheter 1 is positioned at the desired vascular treatment site for deployment of the constrained EPD 22, the trailing portion 6a of the wire 6 is pulled in a proximal direction, as indicated by numeral 11 in FIG. 2B. The pulling motion will pull the looped portion of wire 6 proximally from the distal rim 8 and produce a longitudinal tear or rupture 10 of the constraining sheath 2, beginning at the distal location where wire 6 is secured over the distal rim 8. Once the constraining sheath 2 is torn to a sufficient degree along its length, as shown for example in FIG. 2C, the self-expanding EPD 22 constrained in the constraining sheath 2 is released and permitted to expand into full apposition with the vessel wall, for example, distal of the treatment site.

Figure 1B:
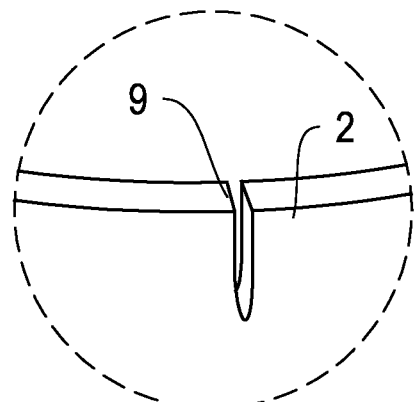
FIG. 1B shows a detail of the delivery tube of FIG. 1A.

To better control tearing of the constraining sheath 2, for example, a relatively small cut or notch 9 may be provided at the distal rim 8 of the constraining sheath 2, as illustrated in FIG. 1B in the detail A. This approach ensures tearing of the constraining sheath 2 preferentially at a desired location by pulling wire end 6a. Tearing of the constraining sheath 2 may be facilitated further by providing the wire 6 with a cutting edge (not shown in the drawing), or by incorporating in the wire 6 abrasive materials, such as diamond dust.

With the illustrated embodiment of the invention, the EPD constrained inside the constraining sheath 2 can be easily deployed due to the relatively small pulling forces required. This EPD deployment approach, for example, avoids the need of overcoming frictional forces associated with relative longitudinal movement between a constrained EPD and a constraining sheath.

Figure 3:
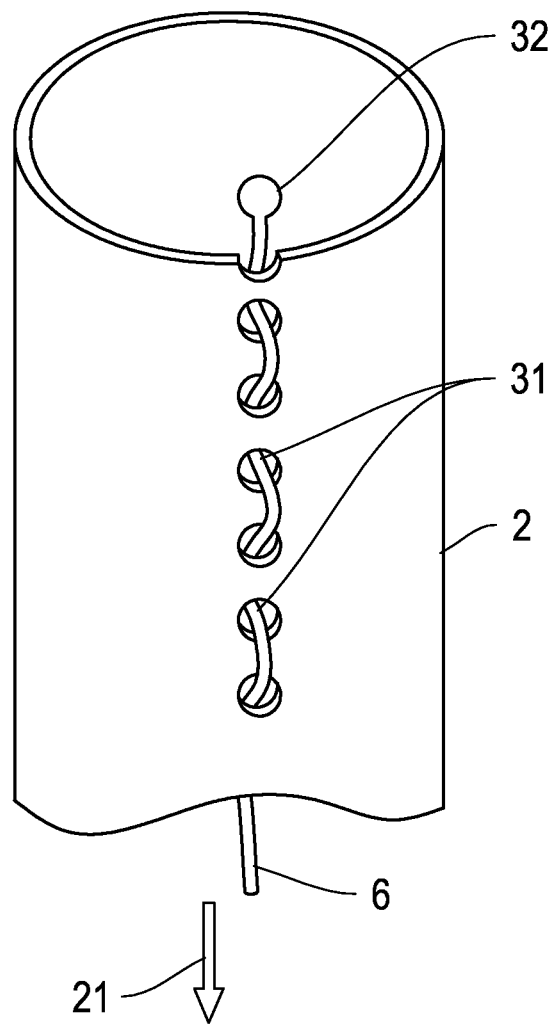
FIG. 3 is a diagrammatic view of another exemplary embodiment of a delivery tube in accordance with various aspects of the invention.

FIG. 3 depicts another design variation for tearing a constraining sheath 2. A series of spaced-apart holes 31 are provided along the length of sheath 2, with a pulling wire 6 being threaded through the holes. The distal end 32 of pulling wire 6 has an enlarged diameter and may incorporate a knife or cutting edge. When pulled in a proximal direction indicated by arrow 21, the enlarged end portion 32 forces the sheath to tear longitudinally in a predictable manner along a line substantially aligned with the holes 31.

Figures 4A, 4B:
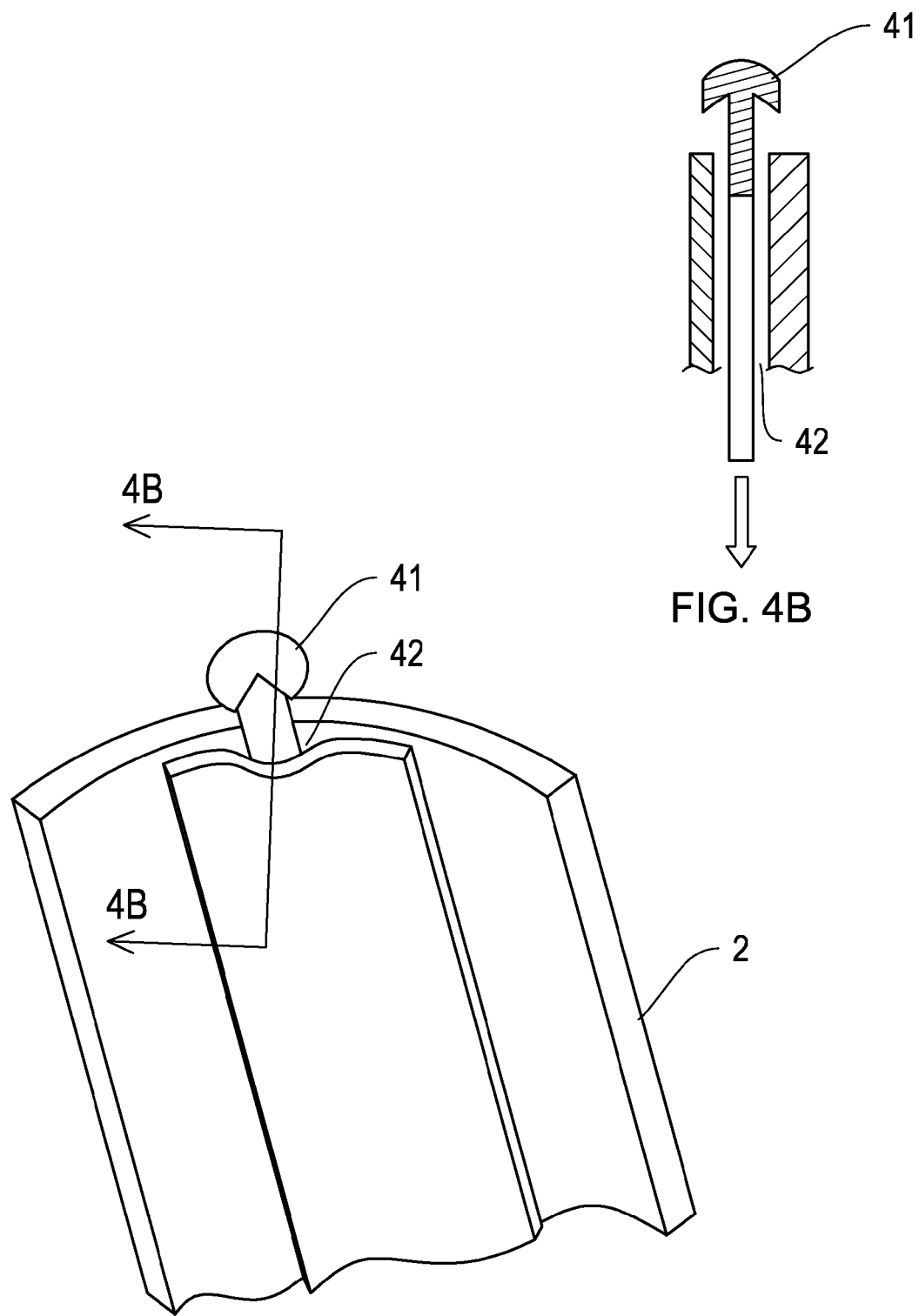
FIGS. 4A and 4B are diagrammatic perspective and cross-sectional views of another exemplary embodiment of a delivery tube in accordance with various aspects of the invention.

FIG. 4A depicts yet another variation of the invention, including a suitably shaped stylet 41 which can be held in a pocket open at both ends and extending longitudinally along the periphery of constraining sheath 2. The stylet can be sickle-shaped, as indicated in the radial cross-sectional view of FIG. 4B, to facilitate tearing of the sheath.

Figure 5:
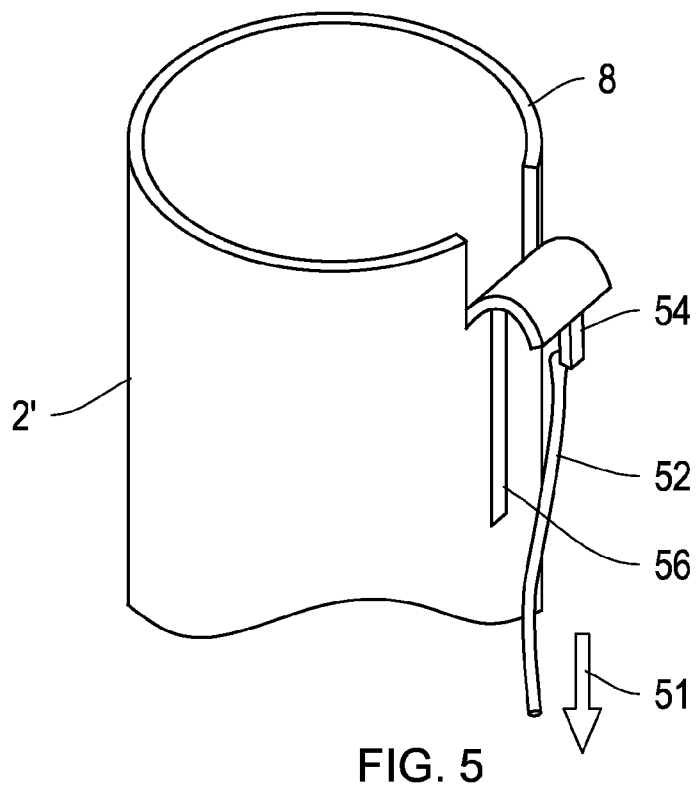
FIG. 5 is a diagrammatic view of yet another exemplary embodiment of a delivery tube in accordance with various aspects of the invention.
Figure 6:
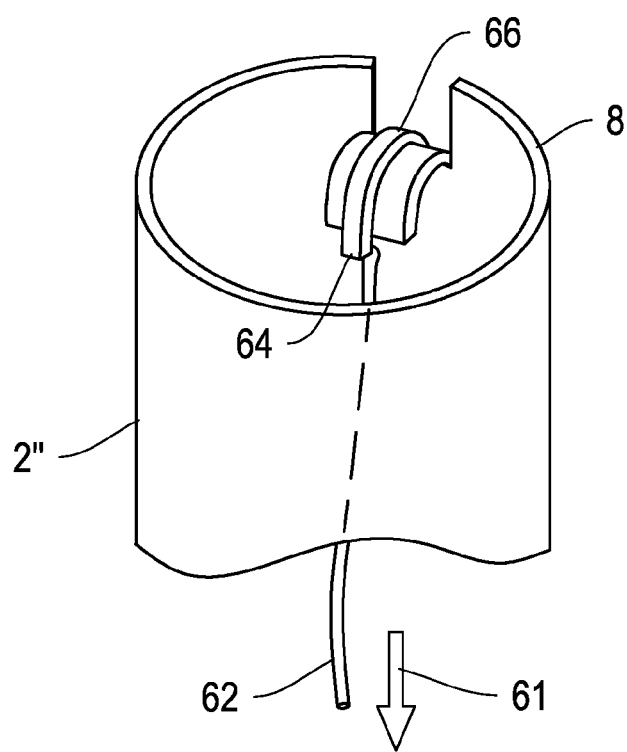
FIG. 6 is a diagrammatic view of another exemplary embodiment of a delivery tube in accordance with various aspects of the invention.

Alternatively, as illustrated in FIG. 5, a pulling wire 52 may be attached to the distal end 8 of constraining sheath 2' and extend proximally outside the constraining sheath 2' from a coupling location 54. The constraining sheath 2' may include an embedded tear strip 56 along which the constraining sheath 2' is longitudinally torn. In a different embodiment illustrated in FIG. 6, a pulling wire 52 is again attached to the distal end 8 of constraining sheath 2", but this time extends proximally inside the constraining sheath 2" from coupling location 64. Like in the embodiment illustrated in FIG. 5, the constraining sheath 2" may include an embedded tear strip 66 along which the constraining sheath 2" is longitudinally torn.

It will be apparent to those skilled in the art that various modifications and variations can be made to the constraining sheath and methods of the present invention without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A delivery catheter for delivering a medical device, the delivery catheter comprising:

a constraining sheath having a proximal end coupled to a distal end of the delivery catheter and a free distal end, said constraining sheath holding the medical device in a constrained state, the constraining sheath including spaced-apart holes arranged longitudinally from the free distal end of the constraining sheath;

a wire threaded through the holes proximally starting from the free distal end of the sheath, the wire having a first free end section extending proximally therefrom and a second free distal end; and a said cutting member at the second free distal end of said wire, said cutting member having a cutting edge directed toward said proximal end such that cutting member tears the constraining sheath longitudinally when a pulling force is applied proximally to the first free end section, thereby releasing the medical device from a constrained configuration to an expanded configuration.

2. The delivery catheter of claim 1, wherein the medical device is an embolic protection device (EPD).

3. The delivery catheter of claim 1, wherein the medical device is a stent.

4. The delivery catheter of claim 1, wherein the cutting member comprises an enlarged end portion, such that when the wire is pulled in a proximal direction the enlarged portion forces the sheath to tear longitudinally in a predictable manner along a line substantially aligned with the longitudinally spaced-apart holes.

5. The delivery catheter of claim 1, wherein the cutting member comprises a sickle-shaped element oriented to present a proximally-directed cutting surface relative to the proximal end of the sheath.

* * * * *